(12) United States Patent
Bruemmer et al.

(10) Patent No.: US 9,188,311 B2
(45) Date of Patent: Nov. 17, 2015

(54) PHOSPHOR DEVICE AND LIGHTING APPARATUS COMPRISING THE SAME

(75) Inventors: Mathias Bruemmer, Wusterwitz (DE); Ulrich Hartwig, Berlin (DE); Nico Morgenbrod, Berlin (DE); Matthias Morkel, Berlin (DE); Henning Rehn, Berlin (DE)

(73) Assignee: OSRAM GmbH, Munich (DE)

( * ) Notice: Subject to any disclaimer, the term of this patent is extended or adjusted under 35 U.S.C. 154(b) by 177 days.

(21) Appl. No.: 13/818,399

(22) PCT Filed: Aug. 24, 2010

(86) PCT No.: PCT/EP2010/062330
§ 371 (c)(1),
(2), (4) Date: Feb. 22, 2013

(87) PCT Pub. No.: WO2012/025144
PCT Pub. Date: Mar. 1, 2012

(65) Prior Publication Data
US 2013/0155649 A1    Jun. 20, 2013

(51) Int. Cl.
*F21V 9/16*    (2006.01)
*G21K 4/00*    (2006.01)
*G03B 21/14*    (2006.01)
*G03B 21/20*    (2006.01)
*H04N 9/31*    (2006.01)
*A61B 1/06*    (2006.01)

(52) U.S. Cl.
CPC . *F21V 9/16* (2013.01); *G03B 21/14* (2013.01); *G03B 21/204* (2013.01); *G21K 4/00* (2013.01); *H04N 9/315* (2013.01); *H04N 9/3158* (2013.01); *H04N 9/3197* (2013.01); *A61B 1/0653* (2013.01); *G21K 2004/06* (2013.01)

(58) Field of Classification Search
CPC ..... G21K 4/00; G21K 2004/06; G03B 21/14; G03B 21/204; F21V 9/16; H04N 9/315
USPC ........................................................ 250/483.1
See application file for complete search history.

(56) References Cited

U.S. PATENT DOCUMENTS

| 7,070,300 B2 * | 7/2006 | Harbers et al. ................ 362/231 |
| 7,651,243 B2 * | 1/2010 | McGuire et al. .............. 362/293 |
| 2005/0046981 A1 | 3/2005 | Karube et al. |

(Continued)

FOREIGN PATENT DOCUMENTS

| CN | 101189543 | 5/2008 |
| CN | 101270854 | 9/2008 |
| CN | 101737722 | 6/2010 |
| DE | 10 2007 037875 | 12/2009 |

(Continued)

OTHER PUBLICATIONS

English translation of WO 2009/021859 to Berben.*

*Primary Examiner* — Marcus Taningco
*Assistant Examiner* — Mindy Vu
(74) *Attorney, Agent, or Firm* — Cozen O'Connor

(57) ABSTRACT

A phosphor device (1) comprising a carrier member (2) having upper and lower faces; a phosphor layer (3) being arranged at the upper face of the carrier member (2), wherein the phosphor layer (3) comprises at least two tiled phosphor zones (R, G, B); an optical transmitting member (4) having a first end face (7) and a second end face (9), the optical transmitting member (4) being arranged at the top portion of the phosphor layer (3), whereby the first end face (7) of the optical transmitting member (4) covers at least a subarea (8) of each of the at least two phosphor zones (R, G, B).

16 Claims, 3 Drawing Sheets

(56) References Cited

U.S. PATENT DOCUMENTS

| | | |
|---|---|---|
| 2006/0238545 A1* | 10/2006 | Bakin et al. ............ 345/613 |
| 2007/0024971 A1 | 2/2007 | Cassarly et al. |
| 2008/0231162 A1 | 9/2008 | Kurihara et al. |
| 2009/0086475 A1 | 4/2009 | Caruso et al. |

FOREIGN PATENT DOCUMENTS

| | | |
|---|---|---|
| TW | 200938771 | 9/2009 |
| WO | WO 2009/021859 | 2/2009 |
| WO | WO 2009/047683 | 4/2009 |
| WO | WO 2010/067291 | 6/2010 |

\* cited by examiner

PHOSPHOR DEVICE AND LIGHTING APPARATUS COMPRISING THE SAME

RELATED APPLICATIONS

This is a U.S. national stage of application No. PCT/EP2010/062330, filed on Aug. 24, 2010.

FIELD OF THE INVENTION

The invention relates to a phosphor device. Furthermore, the invention relates to a lighting apparatus comprising such phosphor device and a method of operation of the lighting apparatus including said phosphor device.

BACKGROUND OF THE INVENTION

Phosphor devices are used in lighting apparatus wherein the phosphor (component or mixture), i.e. a substance with wavelength-converting properties, e.g. a fluorescent or luminescent substance, is remote from the exciting light source. Therefore, they are also called remote phosphor devices. Remote phosphor devices can be used in various lighting applications, e.g. in RGB projection equipment, generating red (R), green (G) and blue (B) light for coloured video projection. Other possible lighting applications comprise medical, architectural or entertainment lighting with coloured or white light.

In prior art remote phosphor devices, such as phosphor wheels, the phosphor is coated on a carrier plate. The phosphor is excited by exciting light, e.g. visible blue laser light (450 nm), impinging on the phosphor layer. The exciting laser light is wavelength-converted by the phosphor to generate light with longer wavelengths (e.g. broad spectral distribution with a peak at approximately 520 nm for green light).

The wavelength-converted light from the phosphor is collected by an optical transmitting member, e.g. an optical collimator such as a lens made of glass, arranged in front of the phosphor.

SUMMARY OF THE INVENTION

It is an object of the present invention to provide a phosphor device with enhanced capabilities for tailoring the spectral properties of the wavelength-converted light emitted by said phosphor device.

According to one aspect of the present invention, adjustment of the colour of the wavelength-converted light is provided.

Another aspect of the present invention is to provide adjustment of the colour temperature of the wavelength-converted white light.

Another aspect of the present invention is to provide adjustment of the colour rendering of the wavelength-converted white light.

The object of the present invention is achieved by a phosphor device comprising: a carrier member having upper and lower faces; a phosphor layer being arranged at the upper face of the carrier member, whereby the phosphor layer comprises at least two tiled phosphor zones; an optical transmitting member having a first end face and a second end face, the optical transmitting member being arranged at the top portion of the phosphor layer, whereby the first end face of the optical transmitting member covers at least a subarea of each of the at least two phosphor zones.

Another aspect of the present invention is directed to a lighting apparatus comprising the phosphor device according to embodiments of the present invention. Finally, protection is also sought for a method of operation of the lighting apparatus comprising the phosphor device according to the present invention.

According to an embodiment of the present invention, the phosphor layer comprises two or more tiled phosphor zones. The term "tiled" in the context of the present invention means that the phosphor zones are close to each other, e.g. adjoin or adjacent to each other. Each phosphor zone com-prises a phosphor component, e.g. a red (R), green (G) or blue light (B) emitting phosphor, or a phosphor mixture, e.g. a white light emitting phosphor mixture. Furthermore, the properties of a phosphor mixture may vary within a phosphor zone.

The phosphor zones may be separated from each other by division bars, preventing cross-talk of the light between the individual phosphor zones. This may also be accomplished by embedding each individual phosphor zone separately into the carrier member. Preferably, the division bars, if any, are as narrow as possible to maximize the optical efficiency of the device.

The exciting light may be visible electromagnetic radiation (VIS), e.g. blue light, as well as ultraviolet (UV) or infrared radiation (IR).

Preferably, the area of the first end face of the optical transmitting member is smaller than the total area of the phosphor layer. The exciting light is wavelength-converted by the phosphors of that particular partial area of the phosphor layer, which is covered by the exciting light, impinging from the first end face of the optical transmitting member. Preferably, the first end face is as close as possible to the phosphor layer to minimize optical losses. Therefore, the partial area of the phosphor layer irradiated by the exciting light is virtually equal to the area of the first end face of the optical transmitting member, projected on the phosphor layer.

Exciting a partial area of the phosphor layer allows for adjusting the spectral properties of the phosphor device by selecting appropriate positions of the first end face of the optical transmitting member on the phosphor layer. An appropriate position may be defined by covering subar-eas of the phosphor zones such that a particular colour of the mixed wavelength-converted light is achieved. Another appropriate position may be defined by covering su-bareas of the phosphor zones, comprising white light phosphor mixtures, such that a particular colour temperature or CRI value of the mixed wavelength-converted white light is achieved.

Furthermore, the phosphor zones are preferably designed such that the respective subareas of the phosphor zones covered by the first end face of the optical transmitting member vary in at least one direction of a relative movement between phosphor layer and optical transmitting member. This concept allows for adjusting the relative pro-portions of the subareas covered by the first end face of the optical transmitting member and, hence, the spectral properties of the mixed light wavelength-converted by the excited subareas of the phosphor zones. For example, the phosphor zones may be formed as stripes tapered or stepped in the direction of relative movement. This concept will be explained later with reference to the drawings in more detail.

Preferably, the phosphor device is configured to enable relative lateral movement between the first end face of the optical transmitting member and the phosphor zones. This may be conducted by translational and/or rotational motion of the optical transmitting member over the phosphor layer or vice versa. This allows not only for pre-setting a favoured spectral property of the phosphor device during manufacturing, but also adjusting another spectral property during operation or even readjusting to compensate degradation of the phosphors of the phosphor device. To this end, the relative position may be con-trolled and adjusted by sensing the resulting light colour in order to achieve a particular target value.

The light, wavelength-converted by the excited subarea of each phosphor zone, is collected and mixed by the optical transmitting member. The optical transmitting member is designed to transmit the light, entering through one end face and leaving through the other end face, by refraction and/or (internal) reflexion. Preferably, the optical transmitting member is elongated and has a polygonal cross section, particularly a triangle or a rectangle. Such a shape of the optical transmitting member allows for proper spatial mixing of the wavelength-converted light collected from the excited subareas of the various phosphor zones. On the contrary, a circular cross section or, similarly, a polygonal cross section with many corners, thereby approximating a circular cross section, may result in poor light mixing, i.e. colour fringes when transmitted to a target area. The mixing of the wavelength-converted light may be further improved by arranging multiple phosphor zones of the same converting colour alternating with phosphor zones of another converting colour, e.g. RGRGR, or RGGBRGGB etc.

The carrier member may be a solid body, e.g. a plate, a block or the like (reflective mode), or a light-transmissive sheet (transmissive mode). In the first case, the carrier member may be made from a material with suitable cooling properties, e.g. a metal such as copper, aluminium or the like, facilitating dissipation of the heat generated by the exciting light when impinging on the phosphor layer. Due to the solid body, the wavelength-converted light is reflected off the phosphor de-vice and collected and mixed by the optical transmitting member. The optical reflectivity of the surface of the carrier member beneath the phosphor layer may be improved, e.g. polished, to enhance the efficiency of the wavelength-conversion. In the other case, heat removal may be facilitated by rotating the light-transmissive phosphor sheet. The sheet may be made of glass or translucent ceramic and, preferably, may be reflective for the wavelength-converted light. Furthermore, the wavelength-converted light is emitted from the rear side of the phosphor device. Therefore, the transmissive type phosphor device further comprises a second optical transmitting member arranged on the rear side of the light-transmissive carrier member for collecting and mixing the wavelength-converted light. In this case, the first optical transmitting member, arranged on the top portion of the phosphor layer, only serves the purpose of guiding the exciting light to the selected subareas of the phosphor zones. Changing the spectral properties may be conducted by translational motion of both optical transmitting members. In each case, the base area of the carrier member may have various shapes, e.g. rectangular or circular. Furthermore, the surface of the carrier member on which the phosphor layer is arranged may be flat or curved.

The phosphor device according to the present invention may be part of a lighting apparatus, further comprising an exciting light source, e.g. a laser, preferably a laser diode or a laser diode array, for emitting exciting light. The exciting light enters the phosphor device through the second end face of the optical transmitting member. After passing through the first end face of the optical transmitting member, the exciting light impinges on the phosphor zones of the phosphor layer where the exciting light is reflected back after being wavelength converted by the phosphors of each irradiated phosphor zone. The various fractions of the wavelength-converted light are collected and mixed by the optical transmitting member after entering its first end face. Thereafter, the mixed light leaves the optical transmitting member through the second end face. The mixed light may be guided and shaped by additional optical devices for fur-ther use in various applications. Further details will be explained in the description of the drawings.

BRIEF DESCRIPTION OF THE DRAWINGS

Embodiments of the present invention will now be described, by way of example, with reference to the accompanying drawings in which:

FIG. 1b is a top view of the embodiment shown in FIG. 1a;

PREFERRED EMBODIMENTS OF THE INVENTION

Figure 1A:
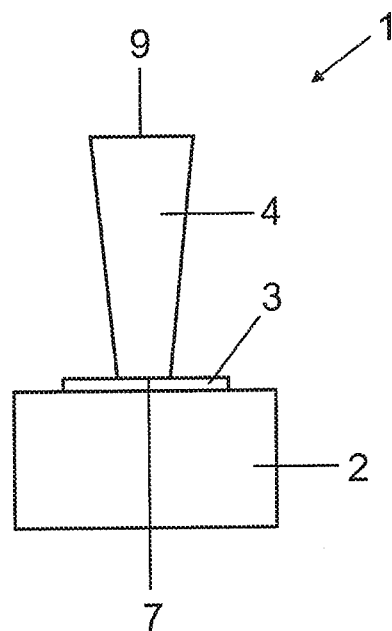
FIG. 1a is a side view of an embodiment of a phosphor device according to the present invention.

In the attached drawings, showing different embodiments of the present invention, the same reference numerals are used for the same or similar features.

Figure 1B:
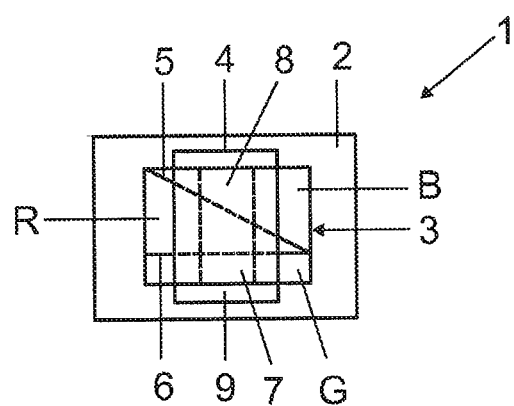
Figure 2:
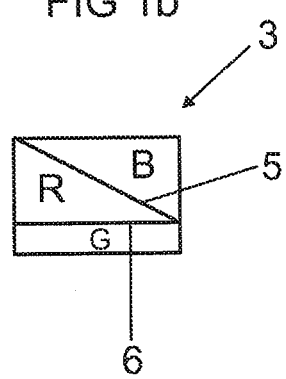
FIG. 2 is a top view of the phosphor layer shown in FIGS. 1a, 1b.

As schematically shown in FIGS. 1a and 1b, a first embodiment of a phosphor device 1 is constructed having a carrier member 2 made of aluminium, a phosphor layer 3, coated on the upper face of the carrier member 2, and an optical transmitting member 4 made of optical glass, preferably quartz glass or BK7 (index of refraction is 1.46 and 1.52, respectively), arranged on the top portion of the phosphor layer 3. Due to the good cooling properties of aluminium, the carrier member 2 also functions as a cooling member. The phosphor layer 3 has a rectangular base area of about 2×10 mm$^2$. If an immersion layer is used on top of the phosphor layer, both optically effective lengths are reduced (divided by the index of refraction of the immersion layer). Typical values for the thickness of the phosphor layer and immersion layer are approximately 0.1 mm for total conversion after double transit of the exciting light according to the reflective mode. The surface portion of the upper face of the carrier member 2 underneath the phosphor layer 3 is polished to enhance its reflectivity. In the following description, reference is also made to FIG. 2, showing, for the sake of clarity, the top portion of the phosphor layer 3 only. The phosphor layer 3 is subdivided into three phosphor zones R, G, B, separated like tiles by two thin separating strips 5, 6, protruding from the upper face of the carrier member 2. The first phosphor zone R comprises a phosphor for emitting red light, e.g. Eu doped YAG. The second phosphor zone G comprises a phosphor for emitting green light, e.g. Ce doped YAG. The third phosphor zone B comprises a phosphor for emitting blue light, e.g. EU doped barium magnesium aluminate (BAM). In different lateral positions of the first end face 7 of the optical transmitting member 4, being in close contact with and covering partial areas 8 of the top portion of phosphor layer 3, different colours of the wavelength-converted light can be achieved. In an utmost left-hand position (not shown), the wavelength-converted light is yellowish. In the central position of the optical transmitting member 4 (cf. FIG. 1a, 1b), the wavelength-converted light is greenish. In an utmost right-hand position (not shown), the wavelength-converted light is turquoise. Furthermore, due to the excellent mixing properties of the tapered optical transmitting member 4, having a rectangular cross-section, the colour distribution of the mixed light passing through the second end face 9 of the optical transmitting member 4 is remarkably uniform. The phosphor device 1, schematically shown in FIGS. 1a, 1b, may further comprise additional means for enabling and controlling the relative motion between optical transmitting member and phosphor layer, but which are not shown for the sake of clarity.

The whole setup is designed for projection purposes illuminating a 0.55" digital mirror device (DMD, also known as Digital Light Processing Unit—DLP®—by Texas Instruments) having an acceptance angle of 12° (half-angle). Therefore, the wavelength-converted light leaving the optical transmitting member should have an angular distribution of below 12°. This is accomplished by the conical transmitting member having a rectangular cross section and a length of approximately 50 to 80 mm. The first end face 7 of the optical transmitting member 4 has a rectangular base area of approximately 2.32×1.74 mm$^2$ (aspect ratio 4:3). The size of the other end face of the transmitting member is then determined according to the Etendue preservation theorem, resulting in 11.2×8.4 mm$^2$.

For other lighting applications, the setup has to be adapted to the specific optical requirements. For instance, for medical endoscopy using fibre bundles of 4.8 mm diameter the acceptance angle is 22° (half-angle) and the aperture is 18.1 mm$^2$. In the case of a Lambertian distribution of the wavelength-converted light, this transforms into a maximum usable area of 2.53 mm$^2$ for the entrance face. This corresponds to an area of 1.4×1.4 mm$^2$ for the first end face of the optical transmitting member having a square cross section. The length of the optical transmitting member may be 25 to 50 mm. For applications using a light guide of 4.8 mm diameter having an acceptance angle of 30° (half-angle), e.g. for automobile head lights, the maximum usable area for the entrance face is 4.5 mm$^2$. This corresponds to an area of 1.75×1.75 mm$^2$ for a square first end face of the optical transmitting member. The length of the optical transmitting member, having a circular second end face, may be 20 to 40 mm.

Figure 3:
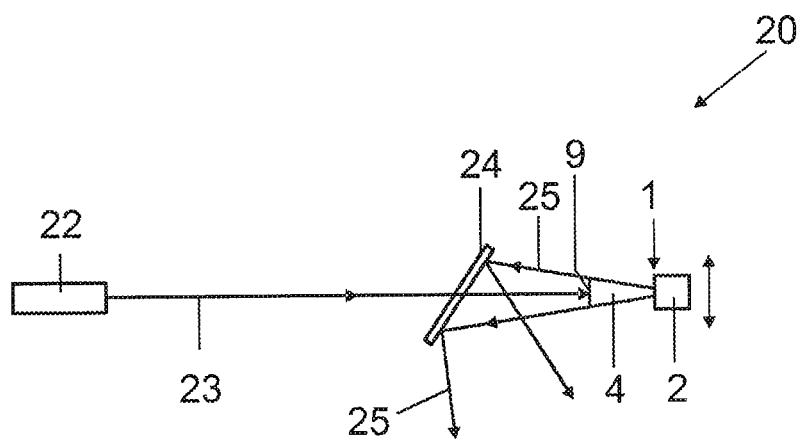
FIG. 3 shows a lighting apparatus comprising a phosphor device as shown in FIGS. 1a, 1b.

FIG. 3 shows a schematic view of a lighting apparatus 20 comprising a phosphor device 1 as shown in FIGS. 1a, 1b. The lighting apparatus 20 may be used for projection applications. The lighting apparatus 20 further comprises at least one laser diode 22, emitting exciting light 23 of a wavelength of about 450 nm, and a dichroitic mirror 24 arranged on the optical axis between the laser diodes 22 and the phosphor device 1. For high power applications, the exciting light source may be a laser array with more than 1 W. The maximum useable laser power may be restricted by degradation of the phosphor layer due to excessive laser power density. The exciting light 23 passes through the dichroitic mirror 24, enters the phosphor device 1 through the second end face 9 of the optical transmitting member 4 and is received by the phosphor layer (not shown) coated on the upper face of the carrier member 2. Depending on the position of the first end face of the optical transmitting member 4 on the phosphor layer, the light wavelength-converted by the excited subareas of the phosphor zones R, G, B is collected and mixed by the optical transmitting member 4, resulting in mixed light with particular spectral properties. If desired, the spectral properties of the mixed wavelength-converted light may be adjusted by relatively moving the optical transmitting member and the phosphor layer. The mixed light exits the second end face of the optical transmitting member 4 and is transmitted to the dichroitic mirror 24. The dichroitic mirror 24 is tilted to re-fleet the mixed wavelength-converted light off the optical axis defined by the beam of the diode laser 22. Depending on the specific application, further optical elements may be involved.

Figure 4:
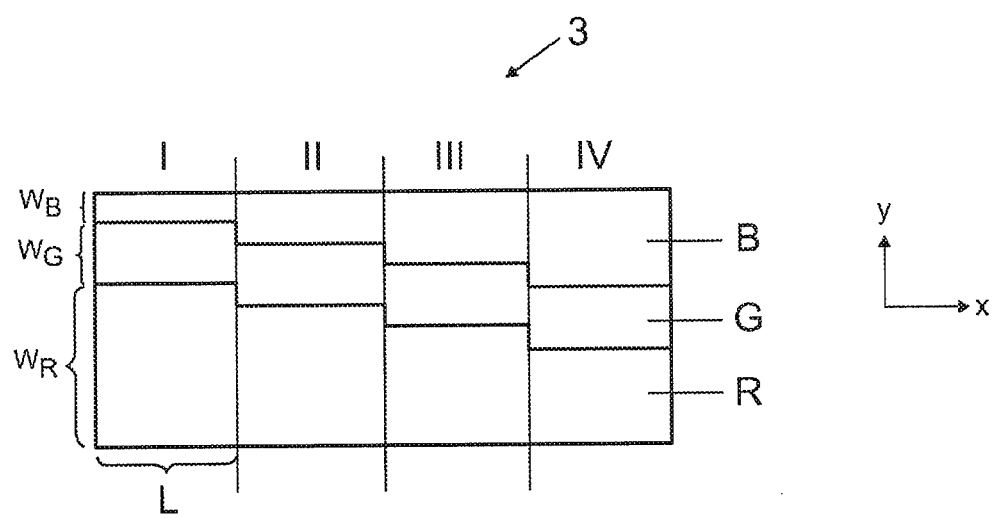
FIG. 4 is a top view of a variation of the phosphor layer shown in FIGS. 1a, 1b.

FIG. 4 shows a variation of the phosphor layer 3 shown in FIGS. 1a, 1b, 2. According to this variation, three strip-like phosphor zones R, G, B for emitting red, green and blue light, respectively, are arranged in parallel. The widths $w_R$, $w_G$, $w_B$ of each phosphor zone varies in a steplike manner along the longitudinal axis x of the phosphor layer 3. Four steps provide for four different positions I, II, III, IV of the optical transmitting member (not shown). The length L of each step equals the length of the first face of the optical transmitting member in the direction of the longitudinal axis x, i.e. along its translational movement from one position to another. Due to the steplike variations of the respective widths of the phosphor zones R, G, B, each position of the optical transmitting member corresponds to another proportion of the subareas of the phosphor zones covered by the optical transmitting member. By this means, four different colour temperatures CT and colour rendering indices CRI of the resulting mixed white light can be achieved. In a further variation of the phosphor layer 3 (not shown), a phosphor for emitting blue light is not required. Instead, the surface of the area corresponding to the phosphor zone B is metallised to reflect the blue exciting light, e.g. 450 nm laser light. However, only lower CRI values can be achieved compared to using a phosphor for emitting blue light. The following table shows various corresponding colour temperatures CCT, the proportions of the subareas R, G, B (B: reflected 450 nm exciting light) required to achieve the CCT values and the resulting CRI values (phosphor conversion efficiencies neglected):

CCT [K] R [%] G [%] B [%] CRI
2700 69,28 24,33 6,39 74
3000 65,27 26,06 8,67 76
3500 59,48 28,05 12,47 79
4000 54,68 29,27 16,05 82
4500 50,72 29,98 19,31 84
5000 47,45 30,36 22,20 85
5500 44,73 30,52 24,75 87
6000 42,46 30,56 26,98 87
6500 40,54 30,51 28,95 88
8000 36,36 30,15 33,50 89

Figure 5:
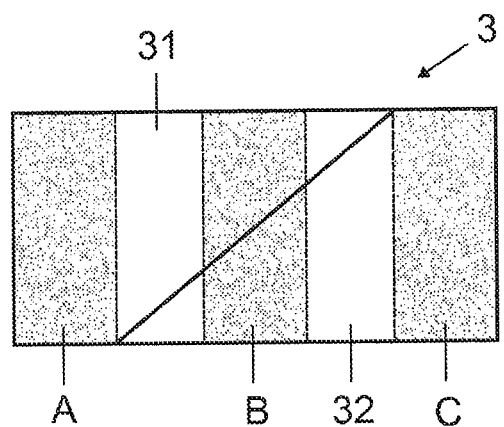
FIG. 5 is a top view of another variation of the phosphor layer shown in FIGS. 1a, 1b.

Another variation of the phosphor layer 3 is shown in FIG. 5. The rectangular phosphor layer 3 is subdivided into two identically shaped halves 31, 32. Each half 31, 32 has the shape of a smaller rectangular and a right-angled triangle extending from a longer side of the smaller rectangular. The upper left half 31 of the phosphor layer 3 consists of a first phosphor mixture for emitting warm-white light (e.g. 3,000 K) and, therefore, is also designated below as the warm-white phosphor zone. The lower right half 32 consist of a second phosphor mixture for emitting cool-white light (e.g. 6,000 K) and, therefore, is also designated below as the cool-white phosphor zone. The area of the rectangular part of each phosphor zone equals the area of the first face of the optical transmitting member. Therefore, at the left most position and at the right most position on the phosphor layer 3, the optical transmitting member covers only a subarea A (hatched area) of the warm-white phosphor zone and a subarea C (hatched area) of the cool-white phosphor zone, respectively. Consequently, at the left most position, the exciting light is wavelength-converted to warm-white light and at the right most position, the exciting light is wavelength-converted to cool-white light. Positions in between both outer positions result in a mixture of warm-white light and cool-white light according to the proportions of the covered subareas of both phosphor zones. At the central position B (hatched area), for instance, the respective proportions is 50:50.

Figure 6:
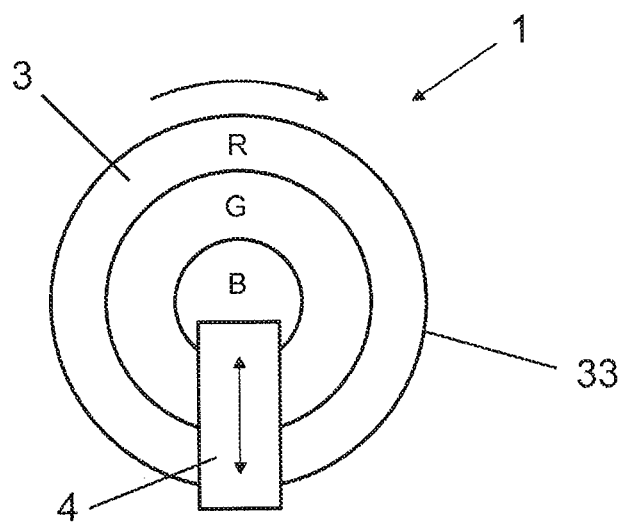
FIG. 6 shows a top view of another embodiment of a phosphor device according to the present invention.

A top view of an alternative embodiment of the phosphor device 1 is schematically shown in FIG. 6. The phosphor layer 3 is arranged on a circular carrier plate 33 and is subdivided into an inner circular zone B and two ring-shaped phosphor zones G, R, concentrically surrounding the inner circular zone B. The circular carrier plate 33 and, hence, the phosphor layer 3 is designed for rotation (indicated by arrow) to facilitate removal of the heat due to the exciting laser light. The optical transmitting member 4 is designed for radial movement over the surface of the phosphor layer 3, facilitating adjustment of the colour of the wavelength-converted mixed light. In a variation (not shown), the phosphor layer is subdivided into two concentric zones, one zone consisting of a warm-white phosphor, the other of a cool-white phosphor. In another variation (also not shown), the phosphor zones are shaped as sectors. In this case, the first face of the optical transmitting member may also be shaped as a sector, covering two or more phosphor zones in steady state (no rotational movement of the carrier plate). To facilitate heat removal the carrier member may be a solid block of metal and may also comprise cooling fins. The optical properties of the wavelength-converted mixed light may then be adjusted by switching the optical transmitting member to cover various sector areas, comprising various proportions of phosphor zones.

The scope of protection of the invention is not limited to the examples given hereinabove. The invention is embodied in each novel characteristic and each combination of characteristics, which includes every combination of any features which are stated in the claims, even if this feature or combination of features is not explicitly stated in the examples.

The invention claimed is:

1. A phosphor device to generate light, the phosphor device comprising:
    a carrier member having upper and lower faces;
    a phosphor layer arranged at the upper face of the carrier member, wherein the phosphor layer comprises at least two tiled phosphor zones;
    an optical transmitting member having a first end face and a second end face, the optical transmitting member being arranged with said first end face at a top portion of the phosphor layer and said second end face remote therefrom, wherein the phosphor device is configured to enable movement of the carrier relative to the optical transmitting member along a longitudinal axis so that the first end face of the optical transmitting member moves longitudinally across the phosphor zones,
    wherein, when the light is generated, the first end face of the optical transmitting member covers at least a subarea of each of the at least two phosphor zones
    wherein
    the phosphor zones are configured such that widths of the phosphor zones vary in a step-like manner so that the proportions of the subareas of the phosphor zones covered by the first end face of the optical transmitting member change by the relative movement of the carrier relative to the optical transmitting member, and
    the length of each step equals a length of the first end face of the optical transmitting member in the direction of the longitudinal axis so that different color temperatures are produced when the optical transmitting member is positioned at each step.

2. The phosphor device according to claim 1, wherein the phosphor zones are separated from each other by division bars.

3. The phosphor device according to claim 1, wherein the phosphor zones are individually embedded into the carrier member.

4. The phosphor device according to claim 1, wherein each phosphor zone comprises a phosphor component or a phosphor mixture.

5. The phosphor device according to claim 4, wherein the phosphor component is any member of the following group: a phosphor for emitting red light, a phosphor for emitting green light, a phosphor for emitting blue light.

6. The phosphor device according to claim 4, wherein the phosphor mixture is suitable for emitting white light.

7. The phosphor device according to claim 1, wherein the optical transmitting member is elongated and has a polygonal cross section.

8. The phosphor device according to claim 1, further comprising a reflective zone arranged adjacent to a phosphor zone.

9. A lighting apparatus comprising:
    a phosphor device according to claim 1;
    an exciting light source for emitting exciting light;
    wherein the phosphor device and the exciting light source are arranged such that the exciting light is enabled to enter the phosphor device through the second end face of the optical transmitting member.

10. The lighting apparatus according to claim 9, wherein the exciting light source comprises a laser light source.

11. A method of operation of a lighting apparatus according to claim 9 comprising the following steps:
    positioning the optical transmitting member such that at least subareas of the at least two phosphor zones of the phosphor layer are covered by the first end face of the optical transmitting member; and
    guiding the exciting light for entering the optical transmitting member through its second end face and for impinging on the phosphor layer through its first end face.

12. The method according to claim 11, further comprising the steps of collecting and mixing the light, wave-length-converted by the area of the phosphor layer irradiated by the exciting light, with the optical transmitting member.

13. The method according to claim 11, further comprising:
    adjusting the spectral properties of the generated light by translational motion of the optical transmitting member relative to the surface of the phosphor layer, thereby covering various subareas of the phosphor zones of the phosphor layer, resulting in various proportions of irradiated subareas of the phosphor zones.

14. The method according to claim 11, further comprising the steps of sensing the resulting light color or corrected color temperature and controlling and adjusting the relative position of the optical transmitting member with respect to the carrier if necessary to achieve a target value.

15. The phosphor device according to claim 1, wherein different color rendering indices are produced when the optical transmitting member is positioned at each step.

16. The phosphor device according to claim 1, wherein the relative movement of the optical transmitting member with respect to the carrier is controlled so as to stop at each step.

* * * * *